United States Patent [19]

Warnke et al.

[11] Patent Number: 4,467,435
[45] Date of Patent: Aug. 21, 1984

[54] INFRARED GAS ANALYZER HAVING DETECTOR ELEMENTS OF DIFFERING TYPES

[75] Inventors: Dale F. Warnke, Irvine; Carl N. Cederstrand, Brea, both of Calif.

[73] Assignee: Beckman Instruments, Inc., Fullerton, Calif.

[21] Appl. No.: 308,874

[22] Filed: Oct. 5, 1981

[51] Int. Cl.³ .......................................... G01N 21/26
[52] U.S. Cl. .................................. 364/497; 250/339; 250/374; 356/51; 364/499; 364/571; 364/572
[58] Field of Search .............................. 364/497-499, 364/509, 525, 571, 572; 250/338-345, 374, 573, 575, 577; 356/51, 72, 73, 435-437, 440

[56] References Cited

U.S. PATENT DOCUMENTS

| | | | |
|---|---|---|---|
| 2,924,713 | 2/1960 | Liston | 250/252.1 |
| 2,957,076 | 10/1960 | Francis | 250/345 |
| 3,539,804 | 11/1970 | Billetdeaux et al. | 250/339 |
| 3,770,974 | 11/1973 | Fertig | 250/344 |
| 3,790,798 | 2/1974 | Sternberg et al. | 250/345 |
| 3,898,462 | 8/1975 | Ishida et al. | 250/344 |
| 3,920,334 | 11/1975 | Steichen et al. | 356/73 |
| 3,979,589 | 9/1976 | Sternberg et al. | 250/345 |
| 4,057,734 | 11/1977 | Barringer | 250/575 |
| 4,156,812 | 5/1979 | Staar | 250/345 |
| 4,233,513 | 11/1980 | Elder | 250/343 |
| 4,236,827 | 12/1980 | Horiba et al. | 250/343 |
| 4,355,233 | 10/1982 | Warnke et al. | 250/345 |
| 4,404,642 | 9/1983 | Rosenthal | 364/498 |

Primary Examiner—Errol A. Krass
Attorney, Agent, or Firm—R. J. Steinmeyer; P. R. Harder; E. C. Jason

[57] ABSTRACT

An improved nondispersive infrared gas analyzer having at least one pneumatic or Luft-type detector and at least one black body type detector located one behind the other along the optical axis of the analyzer. In the preferred embodiment, a black body detector is exposed to radiation from a sample cell through an intervening pneumatic detector. The pneumatic detector absorbs radiation at specific infrared wavelengths, while the black body detector absorbs radiation substantially uniformly at all wavelengths. Signals from the pneumatic detector and the black body detector are combined electronically in an improved signal processing circuit to provide an output signal that is substantially free of the effects of disturbing influences such as infrared source intensity variations, mechanical vibrations and shock, and the presence of interfering compounds.

31 Claims, 8 Drawing Figures (1) $V_{40}(\lambda) = K'\left[Se^{-(a_0C_{ss}+b_0C_{Is})L_s} - Se^{-(a_0C_{ss}+b_0C_{Is})L_s} \cdot e^{-a_0C_{sp}L_p}\right]$ (2) $V_{60}(\lambda) = K_1'\left[Se^{-(a_1C_{ss}+b_1C_{Is})L_s} \cdot e^{-a_1C_{sp}L_p}\right]$ (3) $V_{70}(\lambda) = K_2'\left[Se^{-(a_2C_{ss}+b_2C_{Is})L_s} \cdot e^{-a_2C_{sp}L_p}\right]$ (4) $e^{-x} \cong 1-x$ (5) $V_P \cong KS\left[1-a_0C_{ss}-b_0C_{Is}\right]$ (6) $V_{BB_1} \cong K_1S\left[1-a_1C_{ss}-b_1C_{Is}\right]$ (7) $V_{BB_2} \cong K_2S\left[1-a_2C_{ss}-b_2C_{Is}\right]$ (8) $V_{BB} = \epsilon V_{BB_1} + (1-\epsilon)V_{BB_2}$ (9) $V_Q = V_P - V_{BB}$

(10) $V_Q = S\{K - [\epsilon K_1 + (1-\epsilon)K_2]\}$
$\quad - SC_{Is}\{Kb_0 - [\epsilon K_1 b_1 + (1-\epsilon)K_2 b_2]\}$
$\quad - SC_{ss}\{Ka_0 - [\epsilon K_1 a_1 + (1-\epsilon)K_2 a_2]\}$

(11) $V_Q = -SC_{ss}\{Ka_0 - [\epsilon K_1 a_1 + (1-\epsilon)K_2 a_2]\}$

(12) $V_Q = a'SC_{ss}$

(13) $V_P - V_{BB_1} = (Ka_0 - K_1 a_1)SC_{ss} - (Kb_0 - K_1 b_1)SC_{Is}$

(14) $V_P - V_{BB_1} \cong KaSC_{ss}$

(15) $\dfrac{V_P}{V_{BB_1}} = \dfrac{KS(1-a_0C_{ss}-b_0C_{Is})}{K_1S(1-a_1C_{ss}-b_1C_{Is})}$

(16) $\dfrac{V_P}{V_{BB_1}} \cong 1-a_0C_{ss}$

FIG. 1b

INFRARED GAS ANALYZER HAVING DETECTOR ELEMENTS OF DIFFERING TYPES

BACKGROUND OF THE INVENTION

The present invention relates to nondispersive infrared gas analyzers, and is directed more particularly to gas analyzers in which infrared detectors of differing types cooperate to provide gas concentration readings which are corrected for the effects of a variety of different disturbing influences.

In situations in which the concentration of one component of a sample gas is to be determined, it has long been the practice to make the determination by passing infrared radiation through the sample gas and measuring the infrared radiation absorbed thereby. By restricting the wavelength range to those bands in which the component of interest has distinctive absorption characteristics, the instrument may be made selectively responsive to that particular component of interest.

Instruments of the above-described type may be classified on the basis of the infrared detection devices and schemes employed therein. One type of infrared analyzer includes analyzers in which infrared absorption is measured through the use of black body detectors. These detectors are typically solid-state devices such as thermistor flakes, thermocouples, pyroelectric detectors and the like which are responsive only to the total quantity of infrared radiation to which they are exposed. In analyzers that use this type of detector, the detector is usually illuminated through a narrow band pass filter which causes the detector to respond only to a band of wavelengths that contains absorption bands that are characteristic of the component of interest. One analyzer of this type is shown, for example, in U.S. Pat. No. 3,920,993, issued on Nov. 8, 1975, in the name of C. N. Cederstrand, one of the inventors named in the present application. Another analyzer of this type is shown in U.S. Pat. No. 3,539,804, issued on Nov. 10, 1970, in the name of A. C. Billetdeaux et al. Still another analyzer of this type is shown and described in copending patent application Ser. No. 98,469, entitled "Split Detector", filed on Nov. 29, 1979, in the name of C. N. Cederstrand et al.

Another type of infrared gas analyzer includes analyzers in which detection is accomplished by means of pneumatic detectors, also known as Luft-type detectors. These detectors are typically gas filled, pressure-responsive devices that respond only to the quantity of infrared radiation that is absorbed at the specific wavelengths at which the filling gas has absorption lines. In analyzers that use this type of detector, measurements of the concentration of the component of interest are based on the difference in the pressure inside the detector when a sample gas of unknown composition is present in the sample cell and the pressure inside the detector when a zero gas is present in the sample cell.

Included among analyzers that use pneumatic detectors are analyzers which utilize two or more detectors to reduce or eliminate the effect of some disturbing influence such as ambient mechanical vibrations. An analyzer of the type having a plurality of pneumatic detectors that are arranged to correct for the effects of mechanical vibration and shock is described in U.S. Pat. No. 3,770,974, issued on Nov. 6, 1973, in the name of G. H. Fertig. An analyzer of the type having a plurality of pneumatic detectors that are arranged to compensate for the effect of source intensity variations is shown and described in U.S. Pat. No. 3,130,302, issued on Apr. 21, 1964, in the names of M. D. Liston et al. An analyzer of the latter type which is also said to compensate for the effect of interfering compounds in the sample gas is described in U.S. Pat. No. 2,924,713, issued on Feb. 9, 1960, in the name of M. D. Liston.

Other patents describing analyzers having various types and configurations of pneumatic detectors are shown in U.S. Pat. No. 2,957,076, issued on Oct. 18, 1960, in the name of S. A. Francis; U.S. Pat. No. 3,898,462, issued on Aug. 5, 1975 in the name of Ishida et al; and U.S. Pat. No. 4,156,812, issued on May 29, 1979 in the name of J. Staab.

Prior to the present invention there had also been developed infrared gas analyzers of the type having both black body and pneumatic detectors. In copending application Ser. No. 117,175, now U.S. Pat. No. 4,355,233, entitled "Method and Apparatus for Negating Measurement Effects of Interferent Gases in Nondispersive Infrared Analyzers", filed on Jan. 31, 1980 in the name of C. N. Cederstrand et al, there is described an analyzer in which a plurality of black body detectors having respective band pass filters are positioned between a sample cell and a pneumatic detector. In the latter analyzer, however, the black body detectors are dedicated to developing signals for use in cancelling the effect of respective interfering compounds.

A common feature of error cancellation schemes that utilize pneumatic detectors is that they include at least two pneumatic detectors that are connected in optical series with one another. While the latter configuration is effective in cancelling of the effect of disturbing influences, such as mechanical vibration and shock, that affect similar detectors in a similar way, it is ineffective in cancelling the effect of disturbing influences, such as source intensity variations and the presence of interfering compounds, that affect similar detectors in different ways. This is because the downstream detector is exposed to infrared radiation having a wavelength distribution which has been altered by the selective absorption of radiation by the upstream detector through which it is illuminated. As a result, while the pneumatic detectors themselves may be similar, the fact that they are exposed to beams of radiation having differing wavelength distributions prevents them from producing signals having source and interferent-related error components that may be canceled out in the same way that vibration-related error components may be canceled out.

More generally, the problem with analyzers having like types of detectors is that the need to simultaneously correct for different types of disturbing influences imposes conflicting correction requirements. For disturbing influences such as mechanical vibrations which affect like detectors in the same way, the cascading of like detectors facilitates the correction process. For disturbing influences such as source intensity variations and interfering compounds which affect like detectors differently, on the other hand, the cascading of like detectors hinders the correction process.

If, for example, the output signals from like types of detectors are combined so that vibration-related error components cancel, then the effect of source-related and interferent-related error components do not cancel. Conversely, if like types of detectors are modified to allow the correction of source and interferent related errors, then the ability to compensate for vibration related errors is adversely affected. Thus, prior to the present invention, analyzers that used a plurality of similar infrared detectors could not compensate for different types of disturbing influences simultaneously.

While the analyzer described in the last-mentioned copending application is not subject to the above-described problem, its usefulness is limited in a different way. With one or more black body detectors positioned upstream of the pneumatic detector, there is necessarily a blockage of the radiation that would otherwise fall on the pneumatic detector. This problem is compounded if, as is not unlikely, two upstream black body detectors are used, one to monitor source intensity variations and a second to monitor interferent concentration variations. Significantly, if the upstream black body detectors are made small enough to reduce such problems, the strengths of their output signals and their signal-to-noise ratios becomes unacceptably low. Thus, difficult performance tradeoffs may be necessary.

SUMMARY OF THE INVENTION

In accordance with the present invention, there is provided an infrared gas analyzer which simultaneously corrects for externally caused errors such as ambient mechanical vibration and shock, internally caused errors such as source intensity variations, and sample related errors such as the presence of an interfering compound. One feature of the present invention which contributes to this simultaneous correction is the use of a plurality of detectors of differing types. More particularly, the present invention includes at least one black body detector that is arranged to receive radiation from a sample cell through an upstream pneumatic detector. The analyzer of the invention preferably also includes an additional pneumatic detector that is either not exposed to or not sensitive to radiation transmitted through the sample cell. As will be described more fully presently, this arrangement allows the analyzer to take advantage of both the similarities and the differences between the different types of detectors, as necessary, to eliminate error producing effects of differing types. In this manner there may be eliminated combinations of errors that cannot be eliminated by the use of a plurality of detectors of any one type.

Another feature of the present invention which contributes to the simultaneous correction of a plurality of types of errors is the provision of improved signal processing circuitry. In this circuitry, output signals from detectors of the same and of different types are combined in proportions which cause a plurality of different types of error signal components to cancel one another. In accordance with the present invention the combining of the various signals is accomplished in a manner which assures that the elimination of each type of error signal component occurs without significantly interfering with the elimination of other types of error signal components. In this manner, after all detector output signals have been combined, the resulting signal is simultaneously free of a plurality of different types of errors.

The present invention is particularly suitable for making measurements on gaseous molecules having infrared spectra that include a spectral region in which there are a plurality of relatively widely spaced absorption lines or, more generally, a spectral region in which a relatively small fraction of the region is occupied by absorption features. Such spectral regions include, for example, various sets of the vibrational-rotational bands of many hetero-atomic molecules such as carbon monoxide and hydrogen chloride. The use of these bands, in turn, allows the analyzer of the invention to employ one or more black body detectors which are exposed to the infrared source beam through an upstream pneumatic detector. Because of the differing (approximately complementary) spectral response characteristics of the upstream and downstream detectors, this results in the establishment of a condition in which the pneumatic and black body detectors are effectively responsive to two mutually exclusive portions of a single band of wavelengths. As a result, in spite of the fact that the black body detectors receive infrared radiation only through the pneumatic detector, there are no detrimental interactions between the detector output signals to prevent those output signals from being combined in a way that simultaneously corrects for a plurality of different types of errors.

DESCRIPTION OF THE DRAWINGS

FIG. 1b contains a set of equations that express the relationships governing the operation of the embodiment of FIG. 1.

DESCRIPTION OF THE PREFERRED EMBODIMENTS

Figure 1:
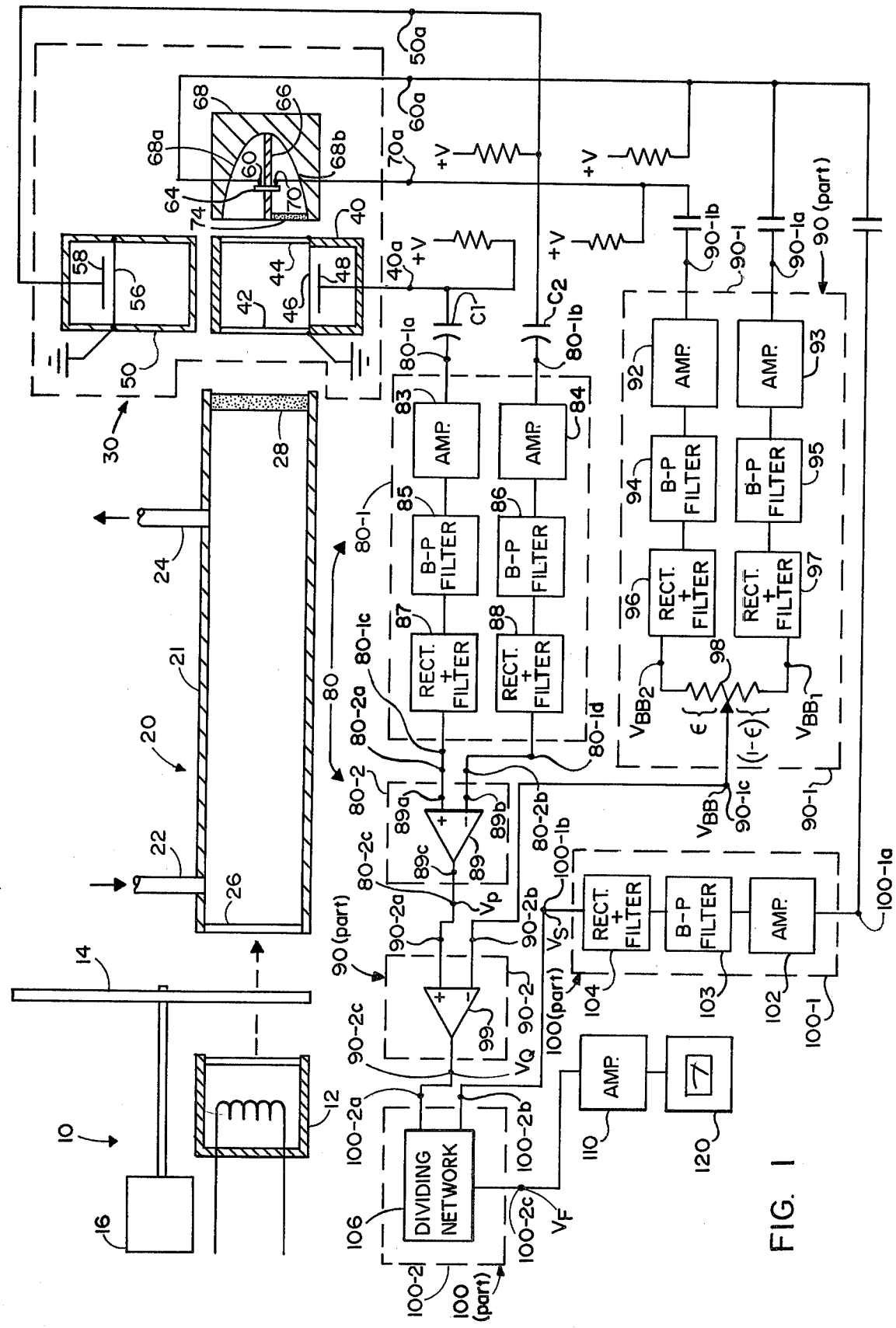
FIG. 1 is a block diagram of one embodiment of the present invention.

Referring to FIG. 1, there is shown a cross-sectional view of the optical portion of an infrared gas analyzer constructed in accordance with the present invention, together with a block diagram of an electronic signal processing circuit suitable for use therewith. The analyzer of FIG. 1 represents the most general or powerful embodiment of the invention and includes apparatus for cancelling (a) the effect of externally caused errors such as mechanical vibration and shock, (b) the effect of internally caused errors such as source intensity variations, and (c) the effect of sample related errors such as the presence of an interfering compound. Other less powerful embodiments of the invention in which certain parts of the apparatus of FIG. 1 are eliminated at the expense of some loss of correcting power will be described later in connection with FIGS. 3 and 4.

Generally speaking, the optical or mechanical portion of the analyzer of FIG. 1 includes a source assembly 10, a sample cell assembly 20 and a detector assembly 30. Together, these assemblies generate a plurality of output signals each of which includes signal components that vary in accordance with the concentration of the component of interest, the intensity of the source radiation, ambient vibrations and the concentration of an interfering compound. The electrical portion of the embodiment of FIG. 1 includes a plurality of error correcting networks 80, 90 and 100, an output signal conditioning network 110 and an output indicator 120. Error correcting networks 80, 90 and 100 combine the various output signals from detector assembly 30, in accordance with the teachings of the present invention, to provide conditioning network 110 and output indicator 120 with a signal from which substantially all of the above-mentioned error components have been eliminated. Thus, the mechanical and electrical portions of the analyzer of FIG. 1 cooperate to provide an output signal that varies substantially only in accordance with the concentration of the component of interest.

As shown in FIG. 1, source assembly 10 includes a source of infrared radiation 12, a chopper blade 14 and a chopper motor 16. Chopper blade 14 serves to periodically interrupt the radiation with which source 12 illuminates sample cell assembly 20, a typical interruption frequency being 10 Hz. These interruptions produce at the detector assembly 30 a modulated signal which may be used, in a manner well known in the art, to reduce both high and low frequency noise in the output signals of detector assembly 30. Because source assembly 10 is conventional in structure and function it will not be described in detail herein.

Sample cell assembly 20 of FIG. 1 includes a generally tubular sample cell 21, having a gas inlet 22 and a gas outlet 24, which serves to contain a flow of the gas to be analyzed. Closing the upstream end of cell 21 is infrared transparent window 26 through which the sample gas is illuminated by source 12. Closing the downstream end of cell 21 is an outlet window 28 which preferably comprises a band pass filter having a pass band that restricts the transmission of infrared radiation through assembly 20 to those portions of the infrared spectrum that contain the absorption lines chosen for use in detecting the component of interest. One example of such a pass band and such a set of absorption lines is illustrated in idealized form in FIG. 2. Except as will be described more fully presently in connection with the choice of a pass band for optical filter 28, sample cell assembly 20 is of a type that is conventional in structure and operation. Accordingly, the structure and operation of assembly 20 will not be described in detail herein.

To the end that the concentration of the component of interest may be determined from the spectral distribution of the radiation transmitted through filter 28, there is provided detector assembly 30. As shown in FIG. 1, detector assembly 30 includes pneumatic detectors 40 and 50, and black body detectors 60 and 70. In accordance with the present invention, the black body detectors are located optically downstream of the pneumatic detectors so that they receive infrared radiation from sample cell assembly 20 only through pneumatic detector 40. As will be described more fully presently, this allows black body detectors 60 and 70 to receive a maximum amount of infrared radiation from source 12, and yet prevents detectors 60 and 70 from obstructing the receipt of infrared radiation by detector 40.

In the embodiment of FIG. 1 first pneumatic detector 40 is of a generally conventional design and includes upstream and downstream infrared transparent windows 42 and 44, respectively, a pressure sensitive flexible electrode 46 that is arranged as a diaphragm and a fixed electrode 48. The latter electrode is connected to output 40a of detector 40. Detector 40 is ordinarily sensitized to the gas of interest by filling the same with an appropriate quantity of that gas. When detector 40 is so filled and connected as shown in FIG. 1, the magnitude of the voltage at output 40a will be determined by the changes in capacitance between electrodes 46 and 48, which changes are dependent upon the strength of the pressure pulses generated in the gas in the detector. The strength of these pulses is, in turn, dependent upon the concentration of the component of interest in sample cell 21. Because of the above-mentioned sensitization, the magnitude of the voltage at detector output 40a reflects the portion of the incident radiation which falls at the wavelengths of the absorption lines shown in FIG. 2, the remaining radiation being transmitted through detector 40 substantially without attenuation.

Pneumatic detector 50, unlike detector 40, has no infrared transparent windows, but does have a gas filling and a pair of electrodes 56 and 58 which are pneumatically similar to those of detector 40. Pneumatic detector 50 is preferably located and oriented so that it receives no radiation from source 12 and yet responds to ambient mechanical vibrations in the same manner as detector 40. This relationship assures that, to the extent that the signal at detector output 40a includes a vibration-related error component, an equal vibration-related error component will appear in the signal at output 50a of detector 50. This condition, in turn, allows the elimination of the vibration-related error component from the output signal of detector 40, within vibration error correcting network 80, without also eliminating the desired signal component therefrom.

To the end that the above-described condition may be established, detector 50 may be located above and parallel to detector 40, as shown in FIG. 1, or may be located beside detector 40 so that flexible electrodes 46 and 56 lie in the same plane or in parallel planes. While the former arrangement is easier to illustrate in FIG. 1, it will be understood that the latter arrangement is preferred in practice because it provides for more precise tracking between the vibration-related error components of the signals at detector outputs 40a and 50a. The former arrangement may also be used, however, provided that the electronic circuitry introduces a 180° phase shift between the outputs of detectors 40 and 50 to compensate for the 180° difference in physical orientation, as shown in FIG. 1.

Figure 1A:
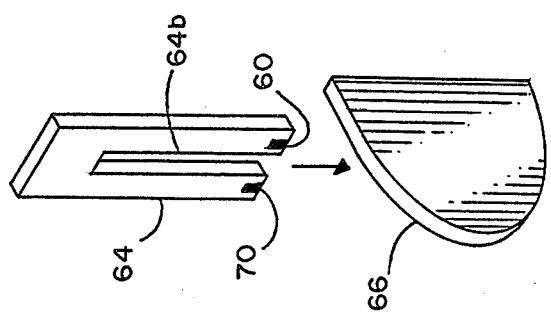
FIG. 1a is a partial perspective view of one part of the embodiment of FIG. 1.

Black body detectors 60 and 70 may each comprise a solid-state infrared responsive device such as a thermistor flake. As is most clearly seen in fragmentary FIG. 1a, detectors 60 and 70 are mounted on opposite arms of a slotted insulating member 64 which is, in turn, mounted on an insulating member 66 by fitting the latter into slot 64b. Members 64 and 66 may then be secured to the interior of a housing 68 to position detectors 60 and 70 to receive radiation through assembly 20. Since the interior of housing 68 comprises a focusing reflective surface, e.g. a parabolic surface, the effect of this detector mounting arrangement is to partition the interior of housing 68 into two focusing elements 68a and 68b, each of which focuses the infrared radiation incident thereon on the detector associated therewith. In this mannner, both of the detectors may be operated at relatively high signal levels and thereby exhibit high signal-to-noise ratios.

Figure 2:
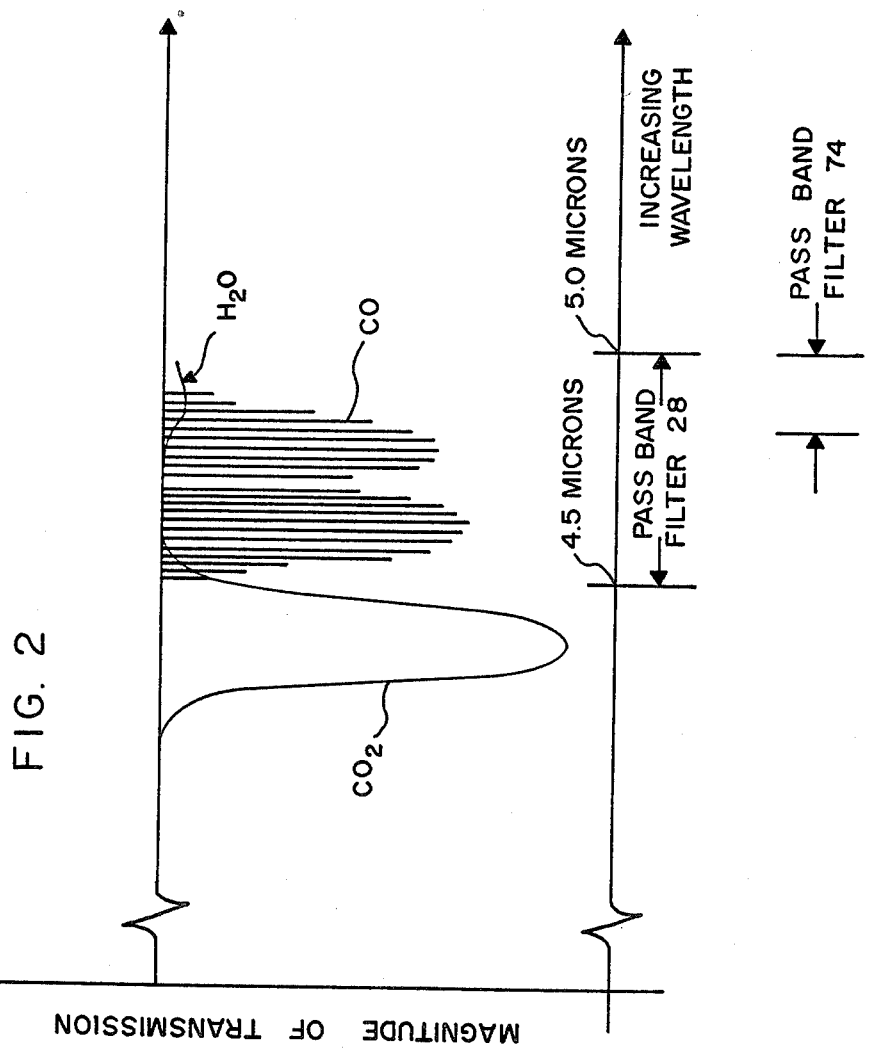
FIG. 2 illustrates the absorption bands that form a part of the absorption spectrum of carbon monoxide.

When detectors 60 and 70 are connected as shown in FIG. 1, detector 60 provides at output 60a thereof an output signal the magnitude of which is dependent upon the total quantity of infrared radiation that is incident theron. Similarly, detector 70 provides at output 70a thereof an output signal the magnitude of which is dependent upon the total quantity of infrared radiation that is incident thereon. For both of detectors 60 and 70 this spectral response is unlike that of pneumatic detector 40 which, as previously described, produces an output signal that is dependent only upon that portion of the infrared energy from source 12 which occurs at the wavelengths of the absorption lines shown in FIG. 2. Significantly, for those gases having absorption spectra of the type shown in FIG. 2, the fraction of the total radiation from source 12 that falls at these absorption wavelengths is such a small fraction of the total energy within the pass band of filter 28 that the magnitudes of the output signals of black body detectors 60 and 70 may (for purposes of certain approximations to be discussed later) be regarded as being substantially independent of the magnitude of the output signal from detector 40. It will be understood that the latter relationship can also be met for gases such as carbon dioxide which do not have absorption spectra of the type shown in FIG. 2, provided that band pass filter 28 is selected to have a relatively broad pass band.

To the end that there may be derived from the outputs of black body detectors 60 and 70 a correction signal that may be used to eliminate the effect of the interferent related error component of the output signal of pneumatic detector 40, a band pass filter 74 having a pass band narrower than that of band pass filter 28 is placed in front of black body detector 70. The pass band of filter 74 is preferably selected so that it transmits to detector element 70 that portion of the radiation in the pass band of filter 28 which contains the strongest absorption band of the interfering compound whose effect is to be eliminated. If, for example, the component of interest is carbon monoxide and water is the principal interferent, filter 74 should be selected so that its pass band includes the bulk of the strongest absorption band of water that is located within the pass band of band pass filter 28, as shown in FIG. 2.

Because detector 70 includes a band pass filter while detector 60 does not, detectors 60 and 70 will produce outputs which are alike in some ways, but different in others. For example, the outputs of detectors 60 and 70 will be alike in that the magnitudes of both will vary directly with the intensity of the radiation from source 12. On the other hand, while both of these outputs will include a component that varies with the concentration of an interfering compound, the sensitivities of detectors 60 and 70 to this interfering compound will differ. More particularly, as a result of the presence of band pass filter 74, changes in the concentration of an interfering compound will produce a greater percentage change in the output of detector 70 than in the output of detector 60. This is because, as shown in FIG. 2, the infrared energy absorbed by water is relatively small compared to the total energy passed by filter 28 and relatively larger compared to the total energy passed through relatively narrower band pass filter 74. The significance of these similarities and differences will be described presently in connection with the signal processing circuitry of FIG. 1.

In accordance with the present invention the signal processing circuitry of FIG. 1 takes advantage of both the differences and the similarities between detectors 40 through 70 to simultaneously eliminate the effect of a plurality of disturbing influences. For example, the signal processing circuitry takes advantage of the differences between like detectors 60 and 70 to eliminate an interferent related error component from the output signal of detector 40. In addition, the fact that source intensity variations have a similar effect on unlike detectors 40 and 60 is taken advantage of to eliminate the source related error component of the output signal of detector 40. Finally, the fact that like detectors 40 and 50 respond in a similar manner to ambient vibrations and differently to changes in the concentration of the component of interest is taken advantage of to eliminate the vibration related error component from the output signal of detector 40. Moreover, the order in which the above-mentioned output signals are combined is predetermined to assure that the making of each error correction does not interfere with the ability of the circuitry to make other needed error corrections.

Before discussing the signal processing circuitry in detail, it is believed advisable to clarify the original or main signal which has the desired component of interest information and from which the various error signal components are removed to produce the desired, final output signal. In the embodiment of FIG. 1 the original or main signal is produced by pneumatic detector 40 and appears at detector output 40a. Also included in this signal, however, is a vibration related error component that results from ambient vibrations and shock, a source related error component that results from source intensity variations, and an interferent error component that results from the presence of an interfering compound in sample cell 21. The manner in which the signal processing circuitry removes the effect of these error components, without adversely affecting the desired signal component, will now be described.

To the end that the vibration related error component may be eliminated from the main signal at detector output 40a, there is provided in FIG. 1 a vibration error correcting network 80 which is connected to detectors 40 and 50 through suitable d-c blocking capacitors C1 and C2. Correcting network 80 is most easily visualized as including a vibration correction signal generating circuit 80-1 and a signal combining circuit 80-2. Of these, signal generating circuit 80-1 receives the raw a-c output signals from detectors 40 and 50 at respective inputs 80-1a and 80-1b thereof, and converts these signals into properly scaled and filtered d-c signals at respective outputs 80-1c and 80-1d thereof. For its part, signal combining circuit 80-2 receives the output signals of generating circuit 80-1 at inputs 80-2a and 80-2b thereof and subtracts those signals to provide at output 80-2c thereof a vibration corrected signal $V_P$ that is substantially free of the above-mentioned vibration-related error component.

In the embodiment of FIG. 1, generating circuit 80-1 includes first and second buffer amplifiers 83 and 84, which are preferably of the type having controllable gains, first and second band pass filters 85 and 86, and first and second rectifier-filter networks 87 and 88. Amplifiers 83 and 84 serve in part to increase the absolute magnitudes of the low level signals received from detectors 40 and 50, respectively. Amplifiers 83 and 84 also serve in part to allow the relative magnitudes of the output signals from detectors 40 and 50 to be properly adjusted. Preferably, the gains of amplifiers 83 and 84 are adjusted so that, when source 12 is turned off and the instrument is subjected to continuous mechanical vibration, the signals at outputs 80-1c and 80-1d of circuit 80-1 are equal to one another. This assures that when these signals are subsequently subtracted within signal combining circuit 80-2, the resulting signal at output 80-2c is zero. This relationship also assures that when the source is turned on and a gas of unknown composition is directed through the sample cell, that the signal at output 80-2c will contain only signal components that are not attributable to vibration effects.

Band pass filter networks 85 and 86, each of which has a pass band which is relatively narrow and which is centered upon the chopping frequency of source assembly 10, serves to eliminate from the output signals of detectors 40 and 50 those signal components which are so high or so low in frequency that they can be assumed to be unrelated to changes in the concentration of the component of interest. The effect of this filtering action is to provide at the output of each of filters 85 and 86 a signal in which the desired component of interest information is conveyed by the peak amplitude of an a.c. waveform having the frequency established by source assembly 10. Because the structure and operation of band pass filters are well known to those skilled in the art, filters 85 and 86 will not be further described herein.

Rectifier-filter networks 87 and 88 serve to receive the a.c. output voltages of filters 85 and 86 and to convert the same to relatively ripple-free d.c. voltages the magnitudes of which are proportional to the strengths of the output signals from detectors 40 and 50. This conversion is desirable because it places the detector output signals in a common or standard form that facilitates the combination thereof with signals from other error correcting networks of FIG. 1, as will be explained more fully presently. Because the structure and operation of rectifier-filter networks 87 and 88 are conventional, these networks will not be described in detail herein.

In view of the foregoing, it will be seen that the vibration correction signal generating circuit 80-1 establishes at output 80-1c thereof an analog d-c signal which is derived from and dependent upon the a-c gas measuring signal from detector 40 (including vibration related components), and establishes at output 80-1d thereof an analog d-c signal which is derived from and dependent only upon the magnitude of the vibration related signal from detector 50. It will also be seen that the magnitude of the signal at output 80-1c is so scaled with respect to the magnitude of the signal at output 80-1d that the latter signal has the proper magnitude for use as a vibration error correction signal.

To the end that the signals produced by circuit 80-1 may be combined to produce vibration corrected signal $V_P$, there is provided a signal combining circuit 80-2. In the embodiment of FIG. 1, combining circuit 80-2 includes a summing amplifier 89 which may comprise an operational amplifier having a non-inverting input 89a connected to circuit input 80-2a, an inverting input 89b connected to circuit input 80-2b and an output 89c connected to circuit output 80-2c. Like amplifiers 83 and 84, amplifier 89 preferably has an adjustable gain. In view of these amplifier connections, it will be seen that the signal at output 89c of amplifier 89 will vary with the algebraic sum of the signals applied thereto by circuit 80-1 and, consequently, that signal $V_P$ at output 80-2c of vibration error correcting network 80 will contain no vibration related error signal. The achievement of this condition represents the completion of the first stage of a multi-stage error correction process the end result of which is the provision of a fully corrected output signal to output indicator 120.

To the end that vibration corrected signal $V_P$ may be further corrected to eliminate the effect of an interfering compound in the sample cell, the signal processing circuitry of FIG. 1 includes an interferent error correcting network 90. The latter network is most easily visualized as including a correction signal generating circuit 90-1 and a signal combing circuit 90-2. Correction signal generating circuit 90-1 is arranged to receive at inputs 90-1a and 90-1b thereof the output signals produced by black body detectors 60 and 70, respectively, and to produce at output 90-1c thereof an interferent correction signal $V_{BB}$ having a magnitude substantially equal to the interferent related error component of vibration corrected signal $V_P$. Signal combining circuit 90-2, which may include a summing amplifier 99, is arranged to receive signals $V_P$ and $V_{BB}$ at respective inputs 90-2a and 90-2b thereof, and to generate at output 90-2c thereof an interferent corrected output signal, i.e., a signal from which the interferent related error component has been eliminated. In accordance with the present invention, the error correcting effect of network 90 is produced without adversely affecting the error correcting activity of the other error correcting networks 80 and 100.

Interferent correction signal generating circuit 90-1 includes adjustable gain amplifiers 92 and 93, band pass filters 94 and 95, and rectifier-filter networks 96 and 97, each of which is electrically and functionally similar to the corresponding networks 83-88 of vibration correction signal generating circuit 80-1. Accordingly, circuits 92-97 will not be separately described herein.

Interferent correction signal generating network also includes a signal mixing element 98 which may take the form of a potentiometer. As will be described more fully presently, mixing element 98 serves to mix an adjustable fraction of a signal $V_{BB1}$ derived from the output of black body detector 70 with a complementarily adjustable fraction of a signal $V_{BB2}$ derived from the output of black body detector 60 to provide at output 90-1c an interferent correction signal $V_{BB}$ having a magnitude that is approximately equal to the interferent related error component of vibration corrected signal $V_P$. This, in turn, allows signal combining circuit 90-2 to combine these signalss to provide at network output 90-2c an interferent and vibration corrected signal $V_Q$, i.e., a signal from which both the interferent related error component and the vibration related error component have been eliminated.

The operation of interferent error correcting network 90 will be described with reference to the set of equations set forth in FIG. 1b. Referring to equations (1) through (3), there are shown the mathematical relationships which express the magnitudes of the output voltages of pneumatic detector 40, and black body detectors 60 and 70, respectively, for a single infrared wavelength $\lambda$. In these equations the quantity S represents the intensity of the radiation from source 12 at wavelength $\lambda$, $C_{SS}$ represents the concentration of the component of interest in the sample cell, $C_{IS}$ represents the concentration of an interfering compound in the sample cell, $L_S$ represents the optical length of the sample cell, $C_{SP}$ represents the concentration of the component of interest in pneumatic detector 40, $L_P$ represents the optical length of pneumatic detector 40, $a_0$, $a_1$ and $a_2$ represent absorption coefficients for the component of interest, $b_0$, $b_1$ and $b_2$ represent absorption coefficients for the interfering compound and $K'$, $K_1'$, and $K_2'$ represent appropriate constants of proportionality. It will be understood that since source 12 produces a multiplicity of wavelengths, the actual voltages produced by detectors 40, 60 and 70 can be computed only by integrating the right-hand sides of equations (1) through (3), with respect to wavelength, over the pass bands of the band filters associated with those equations.

If, as is usually the case, the concentrations of the component of interest and the interfering compound are relatively small, exponential equations (1) through (3) may be simplified through the use of the approximation set forth in equation (4). Based on the use of this approximation, and on the performance of the above-mentioned integration, and on the inclusion of the effect of circuit networks such as 83, 85 and 87, equations (1) through (3) may be rewritten in the form shown in equations (5) through (7). In the latter equations the absence of primes on constants K, $K_1$, and $K_2$ reflect combination of other constant values with the constants $K'$, $K_1'$ and $K_2'$ of equations (1) through (3).

More particularly, the output signal of pneumatic detector 40, after processing by vibration error correcting network 80, appears as a voltage $V_P$ at output 80-2c of network 80, and has a magnitude that is related to source intensity S and to the concentrations of the components of the sample gas in the manner shown in equation (5). Similarly, the output signals of detectors 60 and 70, after processing by circuits 92 through 97, appear as voltages $V_{BB1}$ and $V_{BB2}$, respectively, at the outputs of filter networks 97 and 96, and have the magnitudes indicated by equations (6) and (7). In equations (5) through (7), the coefficients $a_0$, $a_1$ and $a_2$ may be thought of as the sensitivities of the respective detectors to the concentration of the component of interest, and the coefficients $b_0$, $b_1$ and $b_2$ may be thought of as the sensitivities of the respective detectors to the interfering compound.

In accordance with the present invention, the output voltage $V_{BB}$ of network 90-1 is produced by mixing an adjustable fraction of voltage $V_{BB1}$ with an adjustable fraction of voltage $V_{BB2}$ in such a way that the source related error component of signal $V_{BB}$ is unaffected by changes in the relative proportions of signals $V_{BB1}$ and $V_{BB2}$. This relationship is expressed in equation (8) wherein there is introduced a parameter $\epsilon$ such that the sum of the coefficients of signals $V_{BB1}$ and $V_{BB2}$ remains equal to one for all values of $\epsilon$. The latter condition assures that voltages $V_{BB}$ and $V_P$ are both proportional to source intensity S for all values of $\epsilon$. This allows the magnitude of the interferent related error component of voltage $V_{BB}$ to be adjusted until it is equal to that of signal $V_P$. This, in turn, assures that when signals $V_{BB}$ and $V_P$ are algebraically combined in signal combining network 90-2, as shown in equation (9), the resulting signal $V_Q$ is substantially free of interferent related errors and yet remains proportional to infrared source intensity S. In this manner the effect of an interfering compound is eliminated without adversely affecting the ability of the signal processing circuitry to correct for the effect of source intensity variations.

In the embodiment of FIG. 1, the coefficients $\epsilon$ and $(1-\epsilon)$ of equation (8) are provided by applying signal $V_{BB1}$ and $V_{BB2}$ to opposite ends of a mixing potentiometer 98 and by connecting the wiper arm thereof to output 90-1c of circuit 90-1. This connection allows $\epsilon$ to be the percentage of the potentiometer resistance between the wiper arm and one end thereof to serve as $\epsilon$, and the percentage of the potentiometer resistance between the wiper arm and the other end thereof to serve as $(1-\epsilon)$. The fact that mixing element 98 produces an output signal $V_{BB}$ which is related to signals $V_{BB1}$ and $V_{BB2}$ in the manner shown in equation (8) may be verified by summing the voltages between the system ground (to which all voltage of FIG. 1 are referenced) and circuit output 90-1c.

The manner in which interferent error correcting network 90 produces the above results will now be described. Referring to equation (10), there is shown the result of substituting equations (6) and (7) into equation (8), and then substituting the resulting equation and equation (5) into equation (9). Thus, equation (10) gives in its most general form the expression for the output voltage of signal combining circuit 90-2. In the course of deriving equation (10), the terms containing $C_{IS}$ and $C_{SS}$ have been collected, as have the terms which contain neither of $C_{IS}$ and $C_{SS}$. As a result, equation (10) is most easily visualized as including three major parts, each of which is enclosed in brackets in FIG. 1b.

Referring to the first part of equation (10), this expression can be made equal to zero by properly adjusting the gains which the circuit of FIG. 1 provides to signals $V_P$, $V_{BB1}$ and $V_{BB2}$ during calibration with zero gas. This adjustment is easily made since, during the flow of zero gas, the second and third parts of equation (10) must both be equal to zero. During the adjustment process, $K_1$ and $K_2$ are adjusted to be equal to one another, thereby eliminating the effect of changes in $\epsilon$. Thereafter the making of K equal to the values of $K_1$ and $K_2$ assures that the entire expression becomes equal to zero for all values of $\epsilon$ and S. Once so adjusted, the values of K, $K_1$ and $K_2$ are not changed further and, as a result, assure that part one of equation (10) remains equal to zero under all subsequent operating conditions of the instrument.

Referring to the second ($C_{IS}$ containing) part of equation (10), this expression is made equal to zero by properly adjusting the value of $\epsilon$ under a calibration condition in which the instrument is supplied with a gas that includes a quantity of the interfering compound but none of the component of interest. This adjustment is easily made since part one of equation (10) is equal to zero by prior adjustment and since part three of equation (10) is equal to zero because of the absence of the component of interest. Once so adjusted, the value of $\epsilon$ established assures that part two of equation (1) remains equal to zero for all concentrations of the interfering compound.

In view of the foregoing adjustments, it will be seen that the output voltage $V_Q$ of signal combining circuit 90-2 reduces to the expression set forth in equation (11). Since, in the latter equation, each of the terms within the brackets has a constant value that is expressed in units of sensitivity, the entire bracketed portion of equation (11) may be replaced by a new variable $a'$ which is equal to the bracketed portion of equation (11) and which represents the effective sensitivity of the instrument of FIG. 1 as a whole to the component of interest. With the substitution of effective sensitivity $a'$ into equation (11), the latter reduces to equation (12), indicating that voltage $V_Q$ at the output of signal combining circuit 90-2 no longer has either vibration or interferent related error components, but is proportional to source intensity S. Thus, the availability of voltage $V_Q$ represents the completion of the second stage of the multistage correction process contemplated by the present invention.

To the end that the remaining, source related error component of signal $V_Q$ may be eliminated, there is provided in FIG. 1 a source error correcting network 100 that includes a source correction signal generating circuit 100-1 and a signal combining circuit 100-2. Generating circuit 100-1 has an input 100-1a which is connected to receive the output of black body detector 60, and serves to generate at output 100-1b thereof a source correction signal $V_S$ the magnitude of which varies in accordance with source intensity S. Signal combining circuit 100-2 has an input 100-2a which is connected to receive the interferent and vibration corrected signal $V_Q$ from correcting network 90 and an input 100-2b which is connected to receive source correction signal $V_S$ from generating circuit 100-1. Signal combining circuit 100-2 combines these signals to provide at output 100-2c thereof a source corrected signal $V_F$ the magnitude of which is substantially independent of variations in source intensity S. In accordance with the present invention, this signal combining activity is accomplished in a way that assures that the benefits of all previously made corrections are preserved, resulting in a final output signal, $V_F$, which is simultaneously free of vibration, interferent and source related error components.

Source correction signal generating circuit 100-1 includes an adjustable gain amplifier 102, a band pass filter network 103 and a rectifier-filter network 104. Because these networks are electrically and functionally similar to the corresponding networks of generating circuits 80-1 and 90-1, networks 102 through 104 will not be separately described herein.

As previously explained in connection with FIG. 2, the the pass band of filter 28 is selected to meet one of two criteria. For molecules such as CO having a spectral region in which there is sufficient energy in the spaces between the absorption lines to energize black body detectors 60 and 70, the pass band of filter 28 may be quite narrow. For other types of molecules such as $CO_2$, characterized by broader absorption features, the pass band of filter 28 must be broadened to allow the transmission of sufficient energy to energize black body detectors 60 and 70. The meeting of either of these criteria together with the fact that black body detectors produce output signals that vary with the total infrared energy falling thereon, causes the output signal from detector 60 to be approximately independent of the concentration of the component of interest, and to be directly proportional to the intensity of source 12. Similar considerations allow the effect of the interfering compound on signal $V_S$ to be neglected, at least in comparison with the very much larger effect of source intensity variations. Thus, signal $V_S$ at output 100-1b of circuit 100-1 has the the approximate form KS, where K is a constant of proportionality.

In the embodiment of FIG. 1, signal combining circuit 100-2 preferably includes an analog divider 106 the inputs of which are connected so that the signal at network input 100-2a ($V_Q$) is divided by the signal at input 100-2b ($V_S$), and the output of which is connected to output 100-2c. Because the internal structure and operation of analog dividers are well known, the stucture and operation of divider 106 will not be described in detail herein.

Because, as previously explained, the signals $V_Q$ and $V_S$ at the inputs of signal combining circuit 100-2 are each proportional to source intensity S, the source intensity variations in one input signal are canceled by the source intensity variations in the other input signal, causing the resulting signal $V_F$ at output 100-2c to be independent of source intensity S. Significantly, because the signal $V_Q$ is substantially free of vibration and interferent related error components, and because signal $V_S$ is approximately free of vibration and interferent related components, this correction for source errors is accomplished without any appreciable loss of the benefits provided by correcting networks 80 and 90. It will therefore be seen that the signal $V_F$ at the output of source error correcting network 100 is simultaneously corrected for vibration, interferent and source related errors and is suitable for application to output indicator 120, subject only to any desired post-processing, such as amplification by amplifier 110. Thus, the generation or original $V_F$ marks the completion of the final stage of the multi-stage correction process contemplated by the present invention.

In summary, it will be seen that the embodiment of FIG. 1 contemplates the simultaneous elimination of a variety of types of error components by making use of both the similarities and differences between various ones of a variety of different detectors. In addition, it will be seen that the embodiment of FIG. 1 contemplates signal processing circuitry which combines the signals from the above-mentioned detectors in a manner which assures that the elimination of each error component is accomplished without adversely affecting the ability of the circuitry to eliminate other types of error components.

In the embodiment of FIG. 1 error correcting networks 80, 90 and 100 have been drawn in a form which facilitates the understanding of their corrective activity. It will be understood, however, that the various parts of the signal processing circuitry of FIG. 1 may be arranged differently while still accomplishing the above-described results. Voltage $V_P$ will be unaffected, for example, if the inputs of summing amplifier 89 are connected directly to the outputs of amplifiers 83 and 84, and if a single band pass filter and a single rectifier-filter network are connected between the output of that amplifier and network output 80-2c. As another example, the sequential summations performed by summing amplifiers 89 and 99 may be provided by a single, three input summing network connected (through appropriate adjustable resistances) to outputs 80-1c, 80-1d and 90-1c of circuits 80-1 and 90-1. As still another example, band pass filter 103 and rectifier-filter network 104 of circuit 100-1 may be eliminated if the input of amplifier 102 is connected to receive signal $V_{BB1}$ rather than the raw output signal of detector 60. Thus, the practice of the present invention is not limited to the use of signal processing circuitry which is similar in appearance to that of FIG. 1.

In the foregoing description of the embodiment of FIG. 1, each of the analog circuit networks of the signal processing circuitry performs a function of a type that can be easily performed by either an analog or a digital computer. In an analog computer, the programming connections necessary to produce the desired results will largely simply duplicate the fixed connections shown in FIG. 1. In a digital computer, on the other hand, the functions of the various circuit networks of FIG. 1 will be performed as a result of the execution of corresponding sets of program statements, such as subtraction or division subroutines, once the detector output signals have been digitized by suitable analog to digital converters. Accordingly, it will be understood that such computer implementations are entirely equivalent to the hard-wired implementations described herein and are within the contemplation of the present invention.

In particular applications, it may be that the effect of certain types of errors are sufficiently small that part of the full error correcting power of the analyzer of FIG. 1 is unneeded. Alternatively, it may be desirable to accomplish certain of the error corrections described in connection with FIG. 1 in a less precise manner, in the interest of reducing the cost and complexity of the analyzer. One example of a less precise, cost reduced analyzer is shown in the embodiment of FIG. 3.

Figure 3:
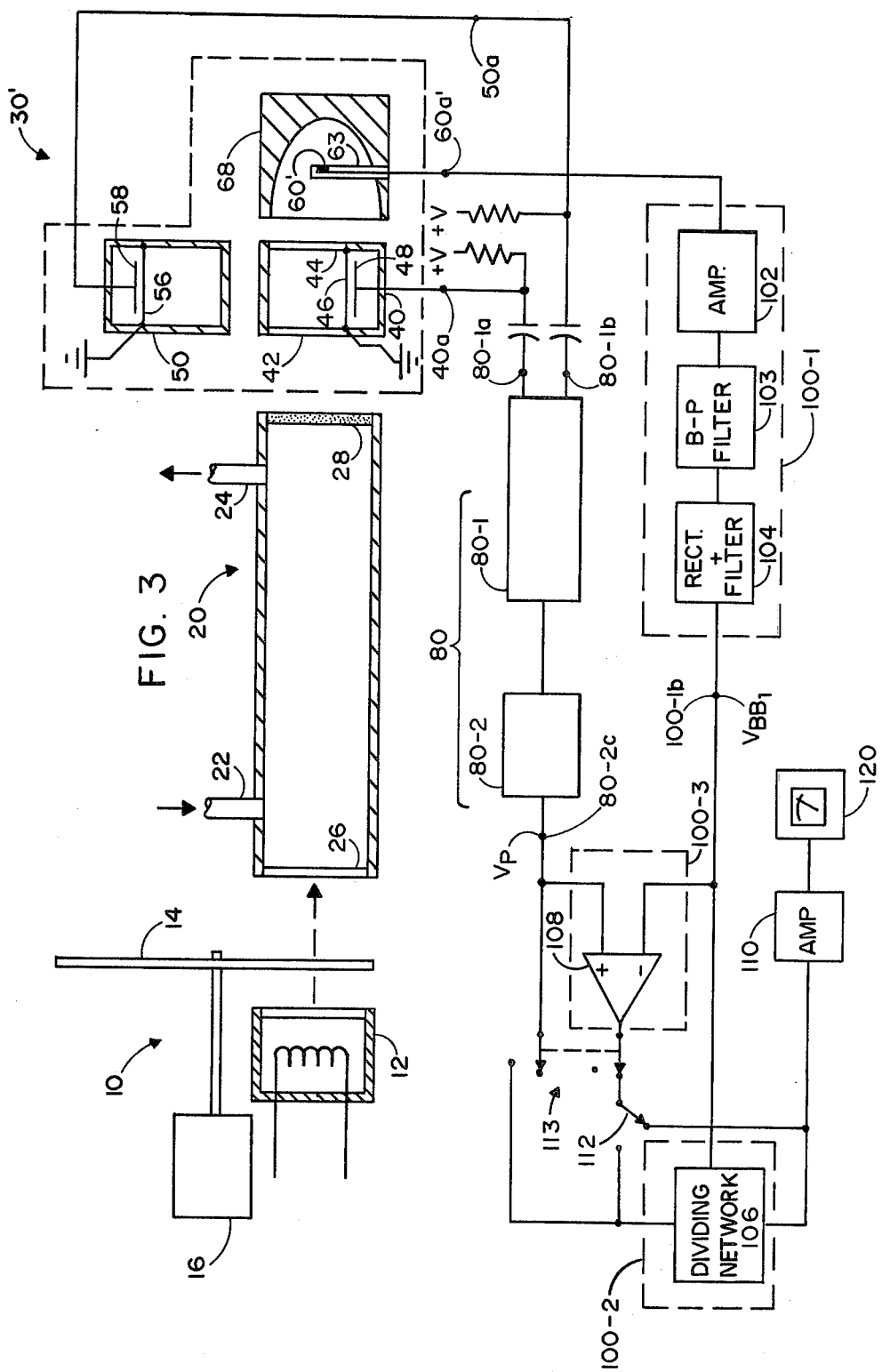
FIG. 3 is a block diagram of an alternative embodiment of the present invention.

The embodiment of FIG. 3 is generally similar to that of FIG. 1, like functioning parts being similarly numbered. The embodiment of FIG. 3 is, however, different from that of FIG. 1 in a number of respects. One difference is that the embodiment of FIG. 3 has a detector assembly 30' that includes only one black body detector 60'. This black body detector may be mounted substantially at the focal point of reflective housing 68 by a suitable mounting element 63.

Another difference is that the embodiment of FIG. 3 does not include circuitry corresponding to correction signal generating circuit 90-1 or signal combining circuit 90-2 of FIG. 1. The absence of these circuits reflects the fact that the embodiment of FIG. 3 has only a single black body detector. The degree to which the absence of these circuits results in a loss of interferent error correcting power will be described presently.

A third difference between the embodiment of FIG. 3 and that of FIG. 1 is that the embodiment of FIG. 3 includes signal combining circuits 100-2 and 100-3 which may be connected to combine the output of correction signal generating circuit 100-1 with the output of vibration error correcting network 80 in any of three different ways. When the selector switches 112 and 113 of FIG. 3 are in the positions shown in FIG. 3, signal combining circuit 100-3 is selected. Under this condition the outputs of circuits 100-1 and 80-2 are combined in an additive manner in circuit 100-3. When, alternatively, switch 112 is moved to a position opposite to that shown in FIG. 3 and switch 113 is maintained in the position shown in FIG. 3, both circuits 100-2 and 100-3 are selected. Under this condition, the outputs of circuits 80-2 and 100-2 are combined in circuit 100-3, with the result being divided by the output of circuit 100-2. When, as a still further alternative, switch 113 is moved to a position opposite to that shown in FIG. 3, signal combining circuit 100-2 is selected. Under this condition, circuit 100-2 combines the outputs of circuits 100-1 and 80-2 by dividing one by the other. The circuits selected by the various states of selector switches 112 and 113 represent choices between three different approximations that may be used in correcting for source and interferent related error components in the signal produced by pneumatic detector 40.

Assume, for example, that selector switches 112 and 113 are in the states shown in FIG. 3, signal combining circuit 100-3 is selected and circuit 100-2 is disconnected. This effectively selects the first of three abovementioned approximations. Under this condition, because signal combining network 100-3 includes a summing amplifier 108, the oppositely phased inputs of which are connected to receive signals $V_P$ and $V_{BB1}$ from circuits 80-2 and 100-1, the output voltage of amplifier 108 will be equal to the difference between those signals. This difference will have the form shown in equation (13) of FIG. 1b. The latter equation is most easily visualized as a form of equation (10) in which the terms contributed by equation (7) are eliminated as a result of the elimination of black body detector 70, and in which $\epsilon$ is made equal to one. It will be understood that gains K and $K_1$ in equation (13) are adjusted to equal one another in the manner described previously in connection with the embodiment of FIG. 1.

Referring to equation (13), it will be seen that the difference signal $V_P - V_{BB1}$ at the output of summing amplifier 108 has a greatly reduced interferent related error component. This is because the sensitivities $b_0$ and $b_1$ of pneumatic detector 40 and black body detector 60 to the interfering compound are approximately equal to one another, causing the right hand portion of equation (13) to be approximately equal to zero. No similar effect occurs for the left hand portion of equation (13) because the sensitivities $a_0$ and $a_1$ of detectors 60 and 40 to the component of interest differ greatly. This, in turn, allows the $K_1 a_1$ term of equation (13) to be neglected, and results in equation (13) being approximated by equation (14). Since the form of the latter equation is similar to that of previously described equation (12), it will be seen that the selection of the first of three abovementioned approximations produces a result that is similar to that of FIG. 1, except for the inability of the first selected circuit to fully correct for variations in source intensity S.

In spite of the fact that the above-described selection does not fully correct for source intensity variations, it does significantly improve the source characteristics of the analyzer. This is because, as shown in equation (14), source intensity S appears only in terms in which it is multiplied by a small number such as $C_{SS}$, the concentration of the component of interest. This represents a substantial reduction in the effect of source intensity variations in comparison to the effect of those variations in equation (5). This is because, in equation (5), source intensity S appears both as a separate term and as a factor of the terms that include gas concentration.

In addition, it will be seen from equation (14) that the output of combining circuit 100-3 will be equal to zero when the concentration of the component of interest is zero, without regard to source intensity S. This is a desirable result since it assures that the "zero" of the analyzer of FIG. 3 has a repeatable value. As may be seen from equation (5), this is not true for an analyzer not having the error correcting circuitry of the invention. Thus, the selection of the first circuit approximation, i.e., the use of only signal combining circuit 100-3, not only reduces the magnitude of source related errors, but also improves the zero characteristics of the analyzer.

In the event that it is desirable to reduce the effect of source intensity variations below the level established by the above-described first circuit selection, the second circuit may be selected by maintaining switch 113 in the position shown in FIG. 3 and by moving switch 112 to a position opposite to that shown in FIG. 3. With this selection the output voltage of circuit 100-3 will be as shown in equation (14) for the reasons described above in connection with the first circuit selection. This voltage is then divided by voltage $V_{BB1}$ in signal combining network 100-2. As a result of this division, the effect of source intensity S is canceled for the reasons given previously in connection with dividing network 106 in FIG. 1. Thus, the second circuit selection gives results that are similar to those of the circuit of FIG. 1. The results are not as precise, however, because the absence of black body detector 70 in FIG. 3 affords only approximate correction of the interferent related error component of the main signal.

Finally, in the event that it is desirable to provide a maximum of source intensity correction with a minimum of signal processing circuitry, this may be accomplished by making the above-described third circuit selection, i.e., by moving switch 113 to a position opposite to that shown in FIG. 3. With this selection, signal $V_P$ is simply divided by signal $V_{BB1}$, yielding the expression shown in equation (15). In addition to affording substantially complete cancellation of source intensity S, the third circuit selection also approximately eliminates the effect of an interfering compound, resulting in a processed signal that has the form shown in equation (16). This is because, as previously explained, sensitivity $a_1$ is small in relation to sensitivity $a_0$ and because sensitivities $b_0$ and $b_1$ are relatively comparable in magnitude. Thus, the third circuit selection, like the first and second circuit selections, simultaneously reduces the effect of vibration, interferent and source related errors. Naturally, if the presence of the constant term "1" in equation (13) is objectionable, this term may be easily removed by connecting a summing amplifier to the output of divider 106 and by including as one input thereto a d-c offset voltage sufficient to eliminate this constant term.

In view of the foregoing it will be seen that, while none of the circuit selections made possible by switches 112 and 113 produces an embodiment of the invention which provides results as precise as those provided by the embodiment of FIG. 1, each circuit selection corrects (at least in part) for all of vibration, source and interferent related errors. Since the degree of correction for each of these types of errors differs for the various states of switches 112 and 113, the embodiment selected by one set of switch states may be more accurate in some applications while the embodiment selected by another set of switch states is more accurate in other applications, depending upon the component of interest, the nature and concentration of the interfering compound, and the stability of the infrared source. Naturally, if it is necessary to have still greater accuracy, the additional accuracy may be obtained by using the more complex circuitry of FIG. 1.

In a commercial version of the gas analyzer of the invention, there will not ordinarily be provided switches of the types shown as 112 and 113 in FIG. 3. Instead, such an analyzer would be expected to include either signal combining circuit 100-2 or signal combining circuit 100-3, or a combination of the two, depending on the intended application. Thus, from a practical standpoint, switches 112 and 113 of FIG. 3 may be regarded as a descriptive device by means of which a number of very similar embodiments may be described in the context of a single drawing.

Figures 3A, 3B, 4:
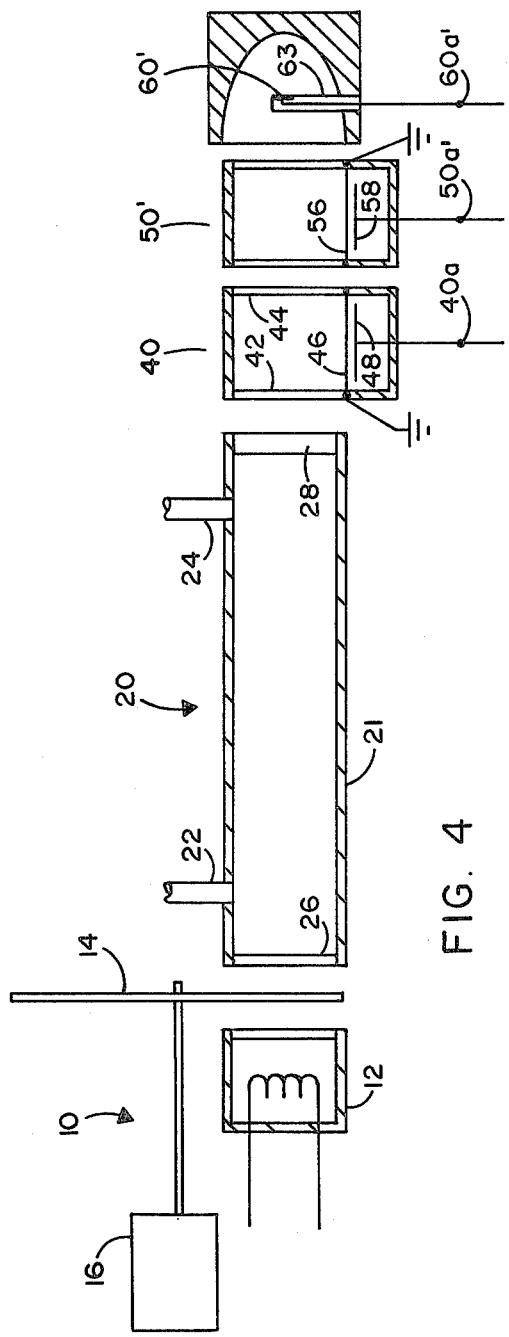
FIGS. 3a and 3b are partial cross-sectional views of alternative black body detectors that may be used in practicing the present invention.
FIG. 4 is a fragmentary block diagram of still another embodiment of the present invention.

Referring to FIGS. 3a and 3b, there are shown fragmentary cross-sectional views of alternative black body detector structures that may be used in practicing the present invention. FIG. 3a, for example, illustrates a black body detector of the type which includes a film pyroelectric type black body detector element having circular metal foils 69a and 69b (upstream foil 69a being blackened) which are separated by a suitable pyroelectric film 69c and which are provided with respective leads 71a and 71b. It will be noted that since foil 69a may have an area comparable to the cross-sectional area of cell 21, no radiation concentrating elements such as mirrors or lenses are needed. In addition, since circular foils 69a and 69b can be radially partitioned into two or more segments having respective pairs of leads, such as 71a and 71b, the black body detector arrangement of FIG. 3a may also be used with split detector arrangements of the type shown in FIG. 1. Thus, in spite of their different appearance, the black body detectors of FIGS. 1, 3 and 3a are functionally equivalent.

Referring to FIG. 3b, there is shown still another type of black body detector having a solid state detector element. In the embodiment of FIG. 3b infrared radiation is concentrated on detector element 62 by glancing reflection from the upstream reflective interior surface of a conical housing 67, rather than by reflection from "downstream" reflective surface, as shown in FIGS. 1 and 3. A concentrating lens may also be included, if desired. The advantage of the embodiment of FIG. 3b is that radiation is concentrated on the detector element without the expense or radiation blockage associated with a mounting element such as 63 of FIG. 3. In all operational respects, however, the detector of FIG. 3b is equivalent to those of FIGS. 1, 3 and 3a.

In the foregoing descriptions of the embodiments of FIGS. 1 and 3, pneumatic detector 50 was described as not being exposed to the radiation passing through sample cell assembly 20. Non-exposure to this radiation is not, however, a requirement for the desired vibration correction. Referring to FIG. 4, for example, there is shown a partial cross-sectional view of an embodiment of the invention in which a pneumatic detector 50' is exposed to the radiation passing through the sample cell and yet provides a signal suitable for use in the above-described vibration error correction. This is accomplished by making detector 50' pneumatically and vibrationally similar to detector 40, but by filling detector 50' with gas that has no absorption bands in the pass band of filter 28. The latter conditions assure that pneumatic detector 50' is unaffected by, i.e., invisible to, infrared radiation and therefore has no adverse effect on the operation of the other detectors 40 and 60' with which it operates. Nevertheless, because detector 50' has a metal diaphragm 56 which is adjacent to an coplanar with metal diaphragm 46 of detector 40, detector 50' is able to provide an output signal that is suitable for use in providing the vibration correction described previously in connection with FIG. 1. In view of these similarities, the embodiment of FIG. 4 will not be described in detail herein.

In each of the previously described embodiments, the penumatic detector assembly was of the type having one pneumatic detector for generating an output signal proportional to the concentration of the component of interest and a second pneumatic detector for providing a signal from which a vibration correction signal could be derived. In the event that the conditions under which the analyzer is used is such that vibration is not a problem, it will be understood that the second pneumatic detector and the electronic circuitry associated therewith may be eliminated. In the embodiment of FIG. 1., for example, this modification would result in the elimination of pneumatic detector 50, amplifier 84, filter 86, rectifier-filter 88 and summing amplifier 89, and in the direct connection of the output of rectifier-filter 87 to input 90-2a of signal combining circuit 90-2. Similar modificatons may be made in the embodiments of FIGS. 3 and 4. In view of their straightforward nature, these modifications will not be further described herein.

In view of the foregoing, it will be seen that the present invention contemplates an analyzer that includes (a) an improved detector arrangement having a plurality of detectors of differing types and (b) improved signal processing circuitry whereby the differences and similarities between like and unlike types of detectors are utilized to simultaneously eliminate the effect of a number of different disturbing influences. It will also be seen that the analyzer of the invention may take a number of different forms, depending on the number of disturbing influences to be corrected for and the accuracy with which the effect of those disturbing influences must be eliminated. Each such form, however, includes at least one pneumatic detector with at least one black body connected optically downstream thereof. This detector structure, together with its associated signal processing circuitry, comprises a single cell analyzer having performance comparable to or better than that of analyzers having separate reference and sample cells.

what is claimed is:

1. In an infrared gas analyzer for providing an output signal that is indicative of the concentration of a component of interest of a sample gas, said analyzer being of the type having an infrared source for generating infrared radiation, a sample cell containing the sample gas, and a band pass filter having a pass band that includes predetermined absorption features of the component of interest, the improvemnt comprising:
   (a) a first pneumatic detector sensitized to the component of interest,
   (b) a black body detector positioned to receive infrared radiation from the source through the sample cell, the band pass filter and the pneumatic detector, and
   (c) signal processing means for combining the signals produced by the pneumatic and black body detectors to correct said output signal for source and interferent related errors.

2. An infrared gas analyzer as set forth in claim 1 wherein the pass band of the band pass filter is selected to include a spectral region in which the energy associated with said absorption features is small in comparison with the total energy in the pass band.

3. An infrared gas analyzer as set forth in claim 1 or 2 in which said absorption features occupy a relatively small fraction of the pass band of the band pass filter and in which the black bdoy detector is adapted to receive substantially all of the infrared radiation that is transmitted through the first pneumatic detector.

4. An infrared gas analyzer as set forth in claim 1 further including a second pneumatic detector which is insensitive to the transmission of infrared radiation through the sample cell and which responds to ambient mechanical vibrations in substantially the same manner as the first pneumatic detector, and means for connecting the second pneumatic detector to the signal processing means to eliminate vibration related errors from the output signal.

5. An infrared gas analyzer as set forth in claim 4 in which the second pneumatic detector is located outside of the optical path of infrared radiation through the sample cell.

6. An infrared gas analyzer as set forth in claim 4 in which the second pneumatic detector is filled with a gas having no absorption bands in said pass band, and in which the second pneumatic detector is connected in optical series with the first pneumatic detector.

7. An infrared gas analyzer as set forth in claim 1 in which the signal processing means comprises means for algebraically summing the signal produced by the pneumatic detector and the signal produced by the black body detector.

8. An infrared gas analyzer as set forth in claim 1 in which the signal processing means comprises means for dividing the signal produced by the pneumatic detector and the signal produced by the black body detector.

9. An infrared gas analyzer as set forth in claim 1 in which the signal processing means comprises means for algebraically summing the signals produced by the pneumatic and black body detectors, and means for dividing the resulting signal by a signal that varies in accordance with the output of the black body dectector.

10. In an infrared gas analyzer for providing an output signal that is indicative of the concentration of a component of interest of a sample gas, said analyzer being of the type having an infrared source for generating infrared radiation, a sample cell containing the sample gas, and a band pass filter having a pass band that includes predetermined absorption features of the component of interest, the improvement comprising:
    (a) a pneumatic detector charged with a quantity of the gas of interest,
    (b) first and second black body detectors each positioned to receive infrared radiation from the source through the sample cell, the band pass filter and the pneumatic detector, said black body detectors exhibiting differing sensitivities to the concentration of an interfering compound in the sample cell, and
    (c) signal processing means for combining the signals produced by the black body detectors and the pneumatic detector to approximately eliminate source and interferent related error components from said output signal.

11. An infrared gas analyzer as set forth in claim 10 wherein the component of interest is a heteroatomic gas, and wherein said absorption features comprise predetermined ones of the rotational absorption lines of the component of interest.

12. An infrared gas analyzer as set forth in claim 10 in which the signal processing means includes:
    (a) interferent error correcting means connected to the first and second black body detectors and to the pneumatic detector for generating an interferent corrected signal the magnitude of which varies in accordance with the concentration of the component of interest in the sample cell, and
    (b) source error correcting means, connected to receive said interferent corrected signal and a signal that is substantially proportional to the output of one of the black body detectors, for generating a source and interferent corrected signal the magnitude of which varies in accordance with the concentration of the component of interest in the sample cell.

13. An infrared gas analyzer as set forth in claim 12 in which the interferent error correcting means includes:
    (a) an interferent correction signal generating network having first and second inputs connected to the first and second black body detectors and an output, and
    (b) an interferent correction signal combining network having a first input connected to the pneumatic detector, a second input connected to the output of the interferent correction signal generating network and an output connected to the source error correcting means.

14. An infrared gas analyzer as set forth in claim 12 or 13 in which the source error correcting means includes:

(a) a source correction signal generating network having an input connected to one of the black body detectors and an output, and (b) a source correction signal combining network having a first input connected to the interferent error correcting means, a second input connected to the output of the source correction signal generating network and an output for providing said source and interferent corrected signal.

15. An infrared gas analyzer as set forth in claim 10 in which the signal processing means includes interferent error correcting means for producing an interferent corrected signal, said correcting means including:

(a) interferent correction signal generating means responsive to the outputs of the black body detectors for generating an interferent correction signal having a magnitude approximately equal to be interferent related error component of the output of the pneumatic detector, and (b) signal combining means for algebraically combining the interferent correction signal with a signal derived from the output of the pneumatic detector to provide a signal from which the interferent related error component has been approximately eliminated.

16. An infrared gas analyzer as set forth in claim 15 in which the signal processing means further includes source error correcting means for substantially eliminating the effect of variations in the intensity of the source, said sorce error correcting means including:

(a) source correction signal generating means responsive to the output of one black body detector for generating a source correction signal having a magnitude approximately equal to the source related error component of the interferent corrected signal, and (b) signal combining means for algebraically combining the source correction signal with the interferent corrected signal to provide said output signal.

17. An infrared gas analyzer as set forth in claim 16 in which the signal combining means of the source error correcting means is an analog divider.

18. An infrared gas analyzer as set forth in claim 15 or 16 in which the interferent correction signal generating means includes mixing means for mixing signals derived from the outputs of the first and second black body detectors to provide an interferent correction signal of the form:

$$V_B = \epsilon V_{BB1} + (1-\epsilon) V_{BB2}$$

where $V_B$ is said interferent correction signal, $V_{BB1}$ and $V_{BB2}$ are signals derived from the outputs of the first and second black body detectors, and $\epsilon$ is a mixing parameter having a value between 0 and 1.

19. An infrared gas analyzer as set forth in claim 15 in which the signal combining means is a summing amplifier.

20. An infrared gas analyzer as set forth in claim 10 in which the signal processing means comprises means for:

(a) deriving an interferent correction signal from the outputs of the black body detectors, (b) deriving a source correction signal from the output of one of the black body detectors, and (c) combining the interferent and source correction signals with a signal derived from the output of the pneumatic detector to provide said output signal.

21. In an infrared gas analyzer for providing an output signal that is indicative of the concentration of a component of interest of a sample gas, said analyzer being of the type having an infrared source for generating infrared radiation, a sample cell containing the sample gas, and a band pass filter having a pass band that includes predetermined absorption features of the component of interest, the improvement comprising:

(a) first and second pneumatic detectors, the first pneumatic detector being sensitized to the component of interest in the sample cell, the second pneumatic detector being filled and mounted so that it produces an output that varies substantially only in accordance with ambient mechanical vibrations, (b) first and second black body detectors having respective first and second sensitivities to the concentration of an interfering compound in the sample cell, (c) means for mounting the first and second black body detectors to receive radiation, from the source, through the sample cell, and (d) signal processing means for combining signals derived from the outputs of the first and second pneumatic detectors, and from the outputs of the first and second black body detectors, to approximately remove from said output signal any vibration related error components, interferent related error components and source related error components which are present therein.

22. An infrared gas analyzer as set forth in claim 21 in which the signal processing means includes:

(a) vibration error correcting means for combining the outputs of the first and second pneumatic detectors to generate a vibration corrected signal, (b) interferent error correcting means for combining said vibration corrected signal and signals derived from the outputs of the first and second black body detectors to generate a vibration and interferent corrected signal, and (c) source error correcting means for combining said vibration and interferent corrected signal with a signal derived from the output of one of the black body detectors to generate said output signal.

23. An infrared gas analyzer as set forth in claim 21 or 22 in which the component of interest is a hetero-atomic gas, and in which said absorption features comprise predetermined ones of the rotational lines of the component of interest.

24. An infrared gas analyzer as set forth in claim 22 in which the interferent error correcting means includes:

(a) interferent error correction signal generating means for generating an interferent correction signal having a magnitude approximately equal to the interferent related error component of the vibration corrected signal, and (b) signal combining means for algebraically combining the vibration corrected signal and the interferent correction signal to produce said vibration and interferent corrected signal.

25. An infrared gas analyzer as set forth in claim 24 in which the interferent error correction signal generating means includes mixing means for producing an interferent correction signal $V_B$ that is related to the signals $V_{BB1}$ and $V_{BB2}$ that are derived from the outputs of the first and second black body detectors, respectively, by the formula:

$$V_B = \epsilon V_{BB1} + (1-\epsilon) V_{BB1},$$

where $\epsilon$ is a mixing parameter having a value between zero and one.

26. An infrared gas analyzer as set forth in claim 22 in which the source error correcting means includes:
 (a) source error correction signal generating means for generating a source correction signal having a magnitude approximately equal to the source related error component of the vibration and interferent corrected signal, and
 (b) signal combining means for algebraically combining the source correction signal with the vibration and interferent corrected signal to generate said output signal.

27. An infrared gas analyzer as set forth in claim 26 in which the signal combining means includes dividing means for dividing the vibration and interferent corrected signal by the source correction signal.

28. An infrared gas analyzer as set forth in claim 22 in which the vibration error correcting means includes:
 (a) vibration error correction signal generating means for generating a vibration correction signal from the output of the second pneumatic detector, and
 (b) signal combining means for algebraically combining the vibration correction signal with a signal derived from the output of the first pneumatic detector to produce said vibration corrected signal.

29. An infrared gas analyzer as set forth in claim 28 in which the signal combining means comprises a summing amplifier.

30. An infrared gas analyzer as set forth in claim 21 in which the signal processing means comprises means for:
 (a) deriving a vibration error correction signal from the outputs of the second pneumatic detector,
 (b) deriving an interferent correction signal from the outputs of the first and second black body detectors,
 (c) deriving a source correction signal from the output of one of the black body detectors, and
 (d) combining the vibration, interferent and source correction signals with a signal derived from the output of the first pneumatic detector to provide said output signal.

31. In an infrared gas analyzer for providing an output signal that is indicative of the concentration of a component of interest of a sample gas, said analyzer being of the type having an infrared source for generating infrared radiation, a sample cell containing the sample gas, and a band pass filter having a pass band that includes predetermined absorption features of the component of interest, the improvement comprising:
 (a) a first infrared detector of the type which absorbs infrared radiation only at predetermined wavelengths,
 (b) a second infrared detector of the type which absorbs infrared radiation substantially without regard to the wavelength thereof,
 (c) means for positioning the second infrared detector to receive infrared radiation from the source through the sample cell, the band pass filter and the first detector, and
 (d) signal processing means for combining the signals produced by the first and second detectors to correct said output signal for source and interferent related errors.

* * * * *